(12) United States Patent
Joo et al.

(10) Patent No.: US 10,183,926 B1
(45) Date of Patent: Jan. 22, 2019

(54) PSEUDO-CERAMIDE COMPOUND AND PREPARATION METHOD THEREFOR

(71) Applicant: AMOREPACIFIC CORPORATION, Seoul (KR)

(72) Inventors: Yung Hyup Joo, Yongin-si (KR); Jae Won Yoo, Yongin-si (KR); Yong Jin Kim, Yongin-si (KR); Ho Sik Rho, Yongin-si (KR); John Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/064,764

(22) PCT Filed: Dec. 15, 2016

(86) PCT No.: PCT/KR2016/014717
§ 371 (c)(1),
(2) Date: Jun. 21, 2018

(87) PCT Pub. No.: WO2017/111387
PCT Pub. Date: Jun. 29, 2017

(30) Foreign Application Priority Data

Dec. 24, 2015 (KR) .......... 10-2015-0186636
Dec. 13, 2016 (KR) .......... 10-2016-0169877

(51) Int. Cl.
*C07D 311/72* (2006.01)
*A61K 8/68* (2006.01)
*A61Q 17/00* (2006.01)
*A61Q 19/00* (2006.01)

(52) U.S. Cl.
CPC .............. *C07D 311/72* (2013.01); *A61K 8/68* (2013.01); *A61Q 17/00* (2013.01); *A61Q 19/00* (2013.01)

(58) Field of Classification Search
CPC ........ C07D 311/72; A61K 8/68; A61Q 17/00; A61Q 19/00
See application file for complete search history.

(56) References Cited

U.S. PATENT DOCUMENTS

| 2001/0056083 | A1 | 12/2001 | Rho et al. |
| 2004/0005282 | A1 | 1/2004 | Gaetani et al. |
| 2009/0010968 | A1 | 1/2009 | Allart et al. |
| 2014/0220139 | A1* | 8/2014 | Park .................... A61K 9/0014 424/489 |
| 2015/0290099 | A1 | 10/2015 | Woo et al. |

FOREIGN PATENT DOCUMENTS

| KR | 10-2001-0093007 A | 10/2001 |
| KR | 10-2001-0104451 A | 11/2001 |
| KR | 10-2013-0030093 A | 3/2013 |
| KR | 10-2014-0070474 A | 6/2014 |
| WO | 2014084676 A1 | 6/2014 |

OTHER PUBLICATIONS

Gonzalez-Garcia et al., "Synthesis and Evaluation of Chromogenic and Fluorogenic Analogs of Glycerol for Enzyme Assays", Helvetica Chimica Acta, 2003, vol. 86, pp. 2458-2470.
International Search Report for Corresponding international Application No. PCT/KR2016/014717 (2 Pages) (dated Apr. 10, 2017).

\* cited by examiner

*Primary Examiner* — Timothy R Rozof
(74) *Attorney, Agent, or Firm* — Lucas & Mercanti, LLP

(57) ABSTRACT

The present invention relates to a pseudo-ceramide compound and a method for preparing the same. The pseudo-ceramide compound of the present invention may provide antioxidant effects, and exhibits improved properties such as high solubility compared to existing natural ceramides and pseudo-ceramide compounds, and therefore, may be included in large quantities in the formulation. Accordingly, the pseudo-ceramide compound may be used in various fields such as cosmetics, medicinal substances, external preparations and foods.

10 Claims, No Drawings

PSEUDO-CERAMIDE COMPOUND AND PREPARATION METHOD THEREFOR

CROSS-REFERENCE TO RELATED APPLICATIONS

This application is a 371 of PCT/KR2016/014717, filed Dec. 15, 2016 which claims the benefit of Korean Patent Application No. 10-2015-0186636 filed Dec. 24, 2015 and Korean Patent Application No. 10-2016-0169877 filed Dec. 13, 2016, the contents of each of which are incorporated herein by reference.

TECHNICAL FIELD

The present invention relates to a novel pseudo-ceramide compound and a method for preparing the same.

BACKGROUND ART

A surface of the human skin is protected by a keratin layer, and among constituents of the keratin layer, keratinocyte lipid forms a layer structure and contributes to maintaining basic functions of the skin.

The keratinocyte lipid is formed with ceramides, cholesterol, free fatty acids and the like. Among these, ceramides play a central role in water retention and barrier function of the keratin layer, and it has been known that, when the ceramide content decreases in the keratin layer, a protective barrier function of the keratin layer deteriorates and various skin diseases become worse.

Meanwhile, it has been reported that, when the keratin layer is damaged by skin aging or external stimuli, and a ceramide content decreases in the keratin layer, ceramides may be supplemented from the outside to restore the skin to a normal condition by restoring the skin's lamellar structure. In view of the above, development for cosmetic compositions including ceramides with the purpose of restoring and maintaining a skin barrier function and enhancing moisturizing power has been actively progressed.

Such ceramides are extracted and used from various animals, plants and microorganisms. However, ceramides present in these animals and plants and microorganisms are extremely small in quantities, and thereby have problems in that extraction is difficult and production costs are high. In addition, nature-derived ceramides have very low solubility for materials such as solvents commonly used in cosmetics, and are difficult to be included in a product in amounts sufficient to exhibit their effects.

As a result, studies on pseudo-ceramide compounds that may replacing natural ceramides have been made. As one example, pseudo-ceramide compounds disclosed in Korean Patent Application Laid-Open Publication No. 2014-0070474 may be included. As above, research and development on pseudo-ceramides having more improved properties while having similar structures and effects to natural ceramides have been consistently required.

PRIOR ART DOCUMENTS

Korean Patent Application Laid-Open Publication No. 2014-0070474, Novel Pseudo-ceramide Compound and Method for Preparing the Same

DISCLOSURE

Technical Problem

As a result of attempts to synthesize pseudo-ceramide compounds having improved properties such as solubility while having a similar structure to natural ceramides, the inventors of the present invention have completed the present invention.

Accordingly, an aspect of the present invention provides a novel pseudo-ceramide compound and a method for preparing the same.

Technical Solution

According to an aspect of the present invention, there is provided a novel pseudo-ceramide compound represented by the following Chemical Formula 1.

In Chemical Formula 1, $R_1$ is a C9 to C23 saturated or unsaturated aliphatic hydrocarbon group unsubstituted or substituted with a hydroxyl group,

[Chemical Formula 1]

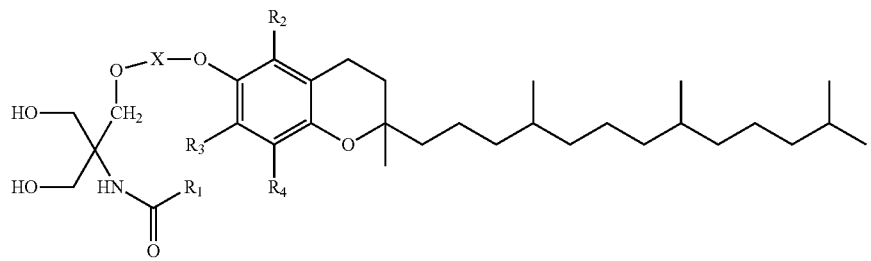

$R_2$, $R_3$ and $R_4$ are the same as or different from each other, and each independently hydrogen or a C1 to C4 alkyl group, and X is

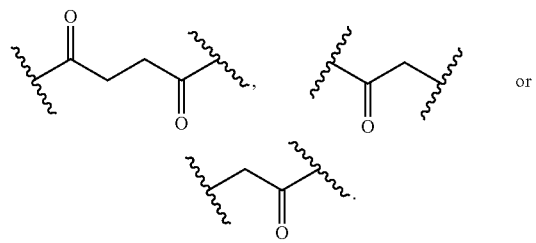

The C9 to C23 saturated aliphatic hydrocarbon group mentioned in the present specification has carbon-carbon bonds formed only as a single bond, may be linear or branched, and examples thereof may include a nonanyl group (C9:0), a decanyl group (C10:0), an undecanyl group (C11:0), a dodecanyl group (C12:0), a tridecanyl group (C13:0), a tetradecanyl group (C14:0), a pentadecanyl group (C15:0), a hexadecanyl group (C16:0), a heptadecanyl group (C17:0), an octadecanyl group (C18:0), a nonadecanyl group (C19:0), an icosanyl group (C20:0), a henicosanyl group (C21:0), a docosanyl group (C22:0) or a tricosanyl group (C23:0).

In addition, the C9 to C23 unsaturated aliphatic hydrocarbon group mentioned in the present specification includes one or more carbon-carbon double bonds or triple bonds, may be linear or branched, and examples thereof may include a nonenyl group (C9:1), a decenyl group (C10:1), an undecenyl group (C11:1), a dodecenyl group (C12:1), a tridecenyl group (C13:1), a tetradecenyl group (C14:1), a pentadecenyl group (C15:1), a hexadecenyl group (C16:1), a heptadecenyl group (C17:1), an octadecenyl group (C18:1), a nonadecenyl group (C19:1), an icosenyl group (C20:1), a henicosenyl group (C21:1), a docosenyl group (C22:1) or a tricosenyl group (C23:1).

As one example, $R_1$ may be a tridecanyl group, a tetradecanyl group, a pentadecanyl group, a hexadecanyl group or a heptadecanyl group, and more specifically, may be a tridecanyl group, a pentadecanyl group or a heptadecanyl group.

In addition, the C1 to C4 alkyl group mentioned in the present specification may be a methyl group, an ethyl group, a propyl group, an isopropyl group or a butyl group, but is not limited thereto.

As one example, $R_2$, $R_3$ and $R_4$ are the same as or different from each other, and may be each independently hydrogen or a methyl group, and more specifically, may be a methyl group.

Specific examples of the compound represented by Chemical Formula 1 may include compounds as follows:

(1) Succinic acid 2-hexadecanoylamino-3-hydroxy-2-hydroxymethyl-propyl ester 2,5,7,8-tetramethyl-2-(4,8,12-trimethyl-tridecyl)-chroman-6-yl Ester, Chemical Formula 11

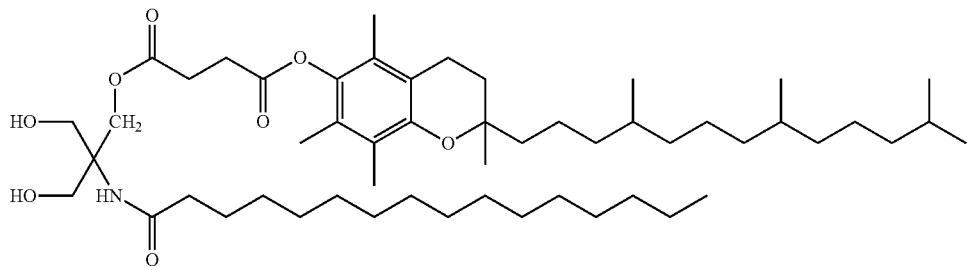

(2) Succinic acid 3-hydroxy-2-hydroxymethyl-2-tetradecanoylamino-propyl ester 2,5,7,8-tetramethyl-2-(4,8,12-trimethyl-tridecyl)-chroman-6-yl Ester, Chemical Formula 12

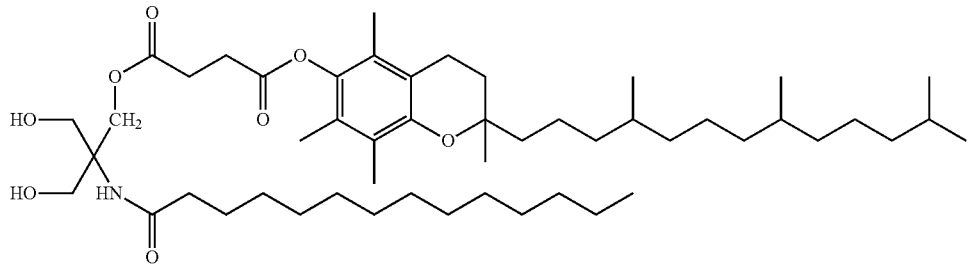

(3) Succinic acid 3-hydroxy-2-hydroxymethyl-2-octadecanoylamino-propyl ester 2,5,7,8-tetramethyl-2-(4,8,12-trimethyl-tridecyl)-chroman-6-yl Ester, Chemical Formula 13

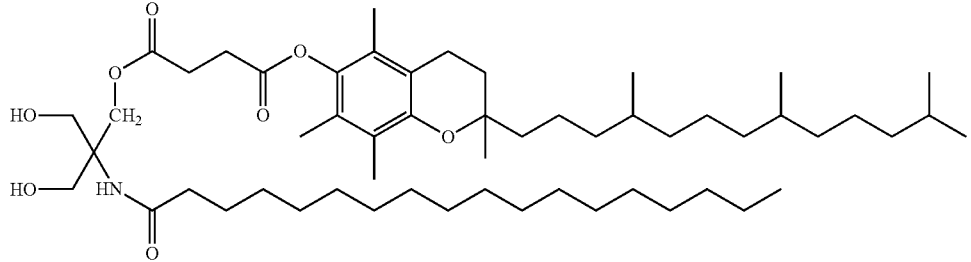

(4) (2-Hexadecanoylamino-3-hydroxy-2-hydroxymethyl-propoxy)-acetic acid 2,5,7,8-tetramethyl-2-(4,8,12-trimethyl-tridecyl)-chroman-6-yl Ester, Chemical Formula 14

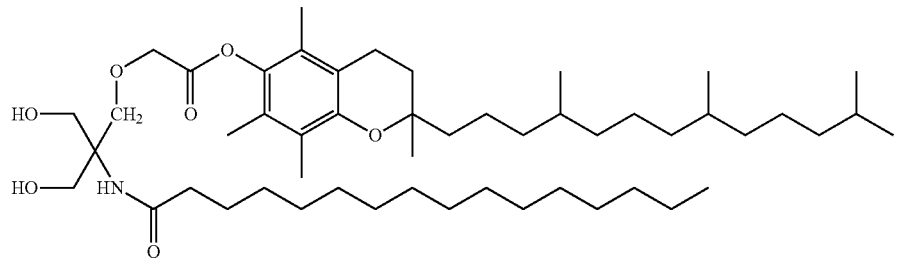

14

(5) (3-Hydroxy-2-hydroxymethyl-2-tetradecanoylamino-propoxy)-acetic acid 2,5,7,8-tetramethyl-2-(4,8,12-trimethyl-tridecyl)-chroman-6-yl Ester, Chemical Formula 15

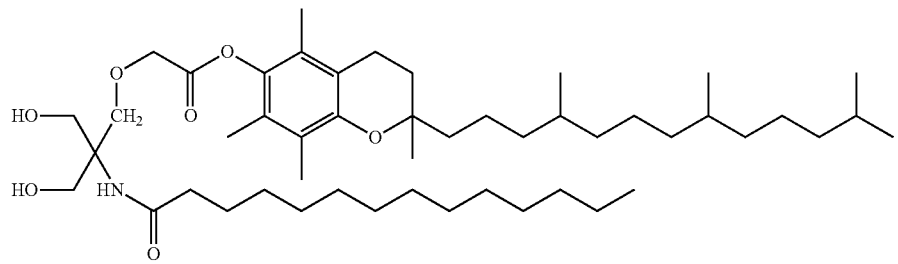

15

(6) (3-Hydroxy-2-hydroxymethyl-2-octadecanoylamino-propoxy)-acetic acid 2,5,7,8-tetramethyl-2-(4,8,12-trimethyl-tridecyl)-chroman-6-yl Ester, Chemical Formula 16

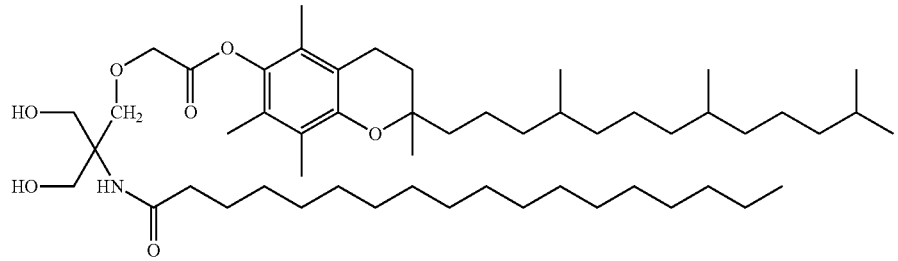

16

(7) [2,5,7,8-Tetramethyl-2-(4,8,12-trimethyl-tridecyl)-chroman-6-yloxy]-acetic acid 2-hexadecanoylamino-3-hydroxy-2-hydroxymethyl-propyl Ester, Chemical Formula 17

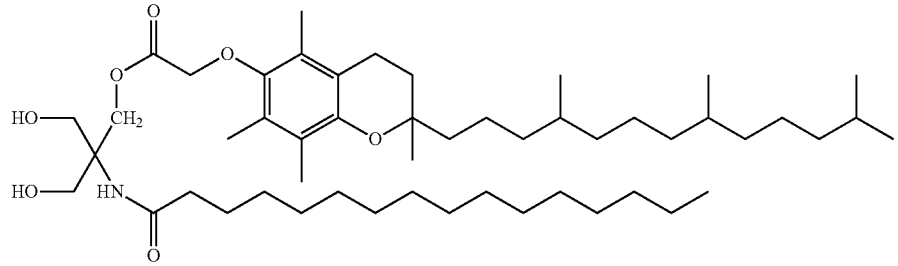

17

(8) [2,5,7,8-Tetramethyl-2-(4,8,12-trimethyl-tridecyl)-chroman-6-yloxy]-acetic acid 3-hydroxy-2-hydroxymethyl-2-tetradecanoylamino-propyl Ester, Chemical Formula 18

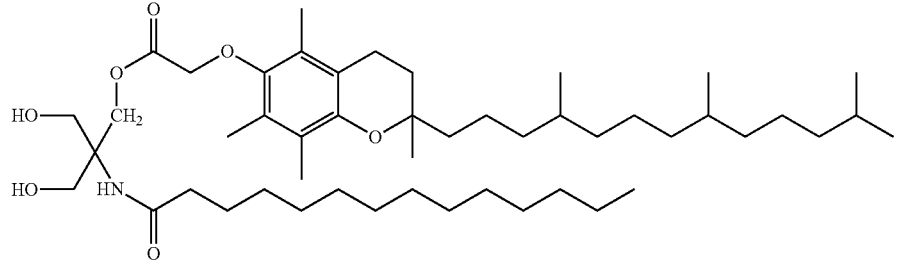

18

(9) [2,5,7,8-Tetramethyl-2-(4,8,12-trimethyl-tridecyl)-chroman-6-yloxy]-acetic acid 3-hydroxy-2-hydroxymethyl-2-octadecanoylamino-propyl Ester, Chemical Formula 19

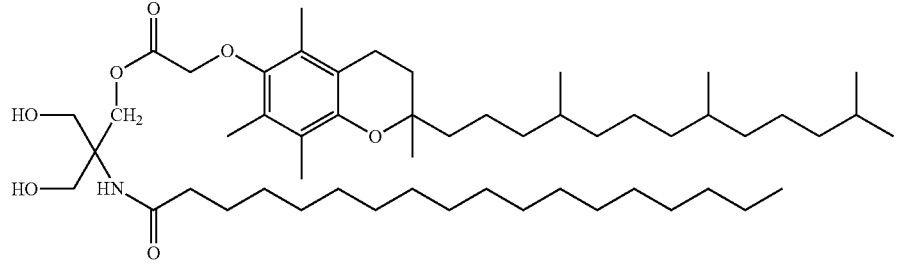

19

The compound of Chemical Formula 1 according to the present invention forms an asymmetric molecular structure by including a tocopherol moiety, and is expected to have improved properties such as high solubility compared to existing pseudo-ceramide compounds having a symmetric structure. In addition, when the compound of Chemical Formula 1 is partially decomposed at an active site to release the tocopherol moiety, an antioxidant effect is provided to prevent aging of biological membranes.

Particularly, the compound of Chemical Formula 1 of the present invention includes all isomers unless particularly mentioned otherwise. The isomer includes a structural isomer and a stereoisomer, and herein, the stereoisomer includes both an optical isomer such as an R/S isomer and a diastereomer such as an E/Z isomer.

According to another aspect of the present invention, there is provided a method for preparing the pseudo-ceramide compound of Chemical Formula 1.

The method for preparing the compound of Chemical Formula 1 of the present invention may be represented by the following Reaction Formula 1, and includes obtaining a compound of Chemical Formula 4 by reacting a compound of Chemical Formula 2 with a compound of Chemical Formula 3; and obtaining the compound of Chemical Formula 1 by deprotecting the compound of Chemical Formula 4.

X is

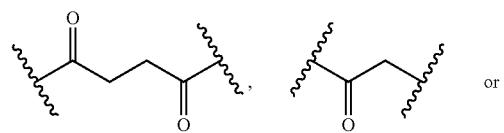

or

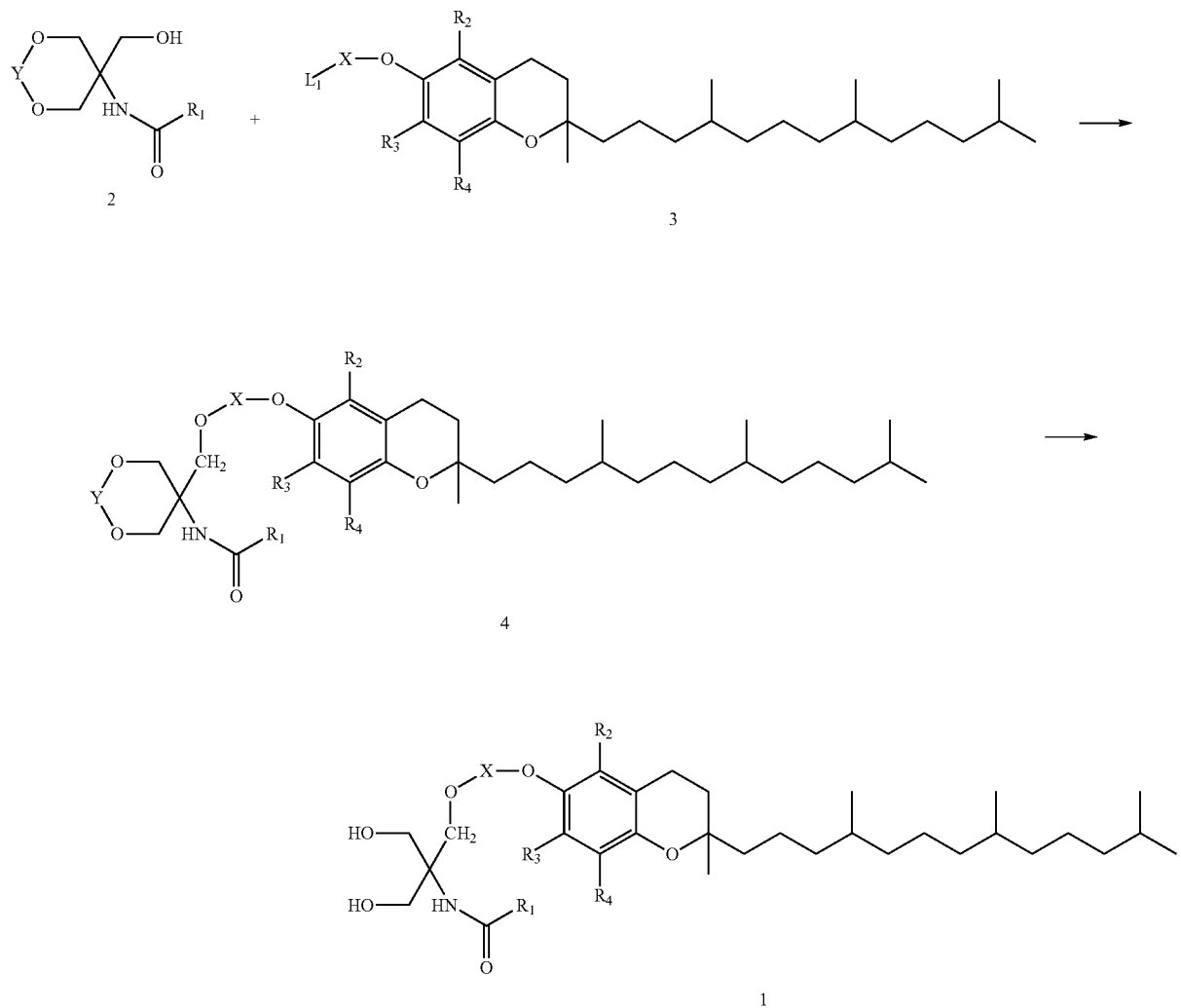

In Reaction Formula 1, $R_1$ is a C9 to C23 saturated or unsaturated aliphatic hydrocarbon group unsubstituted or substituted with a hydroxyl group, $R_2$, $R_3$ and $R_4$ are the same as or different from each other, and each independently hydrogen or a C1 to C4 alkyl group, -continued

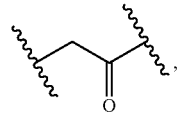

Y is alkylidene, ethylidene, isopropylidene, cyclohexylidene, benzylidene or p-methoxybenzylidene, and $L_1$ is a leaving group, and examples thereof may include a hydroxyl group, halogen, a C1 to C4 acyloxy group, a C1 to C4 alkyl carbonate group or a C1 to C4 alkoxy group.

Herein, the halogen may be F, Cl, Br or I, the C1 to C4 acyloxy group may be formate, acetate, propionate or butanoate, the C1 to C4 alkyl carbonate group may be methyl carbonate, ethyl carbonate, propyl carbonate or butyl carbonate, and the C1 to C4 alkoxy group may be methoxy, ethoxy, propoxy, isopropoxy or butoxy.

Hereinafter, each step will be described.

(1) Preparation of Compound of Chemical Formula 4

As shown in the following Reaction Formula 2, a compound of Chemical Formula 4 may be prepared through a reaction of a compound of Chemical Formula 2 with a compound of Chemical Formula 3.

using a method represented by Reaction Formula 3. In other words, the compound of Chemical Formula 2 may be prepared by preparing a compound of Chemical Formula 6 through introducing a 1,3-diol protecting group to tris(hydroxymethyl)aminomethane, (2-amino-2-hydroxymethyl-propane-1,3-diol, Chemical Formula 5), a starting material, and then reacting the compound of Chemical Formula 6 with a compound of Chemical Formula 7 having a fatty acid group. Herein, tris(hydroxymethyl)aminomethane hydrochloride may be used as the starting material.

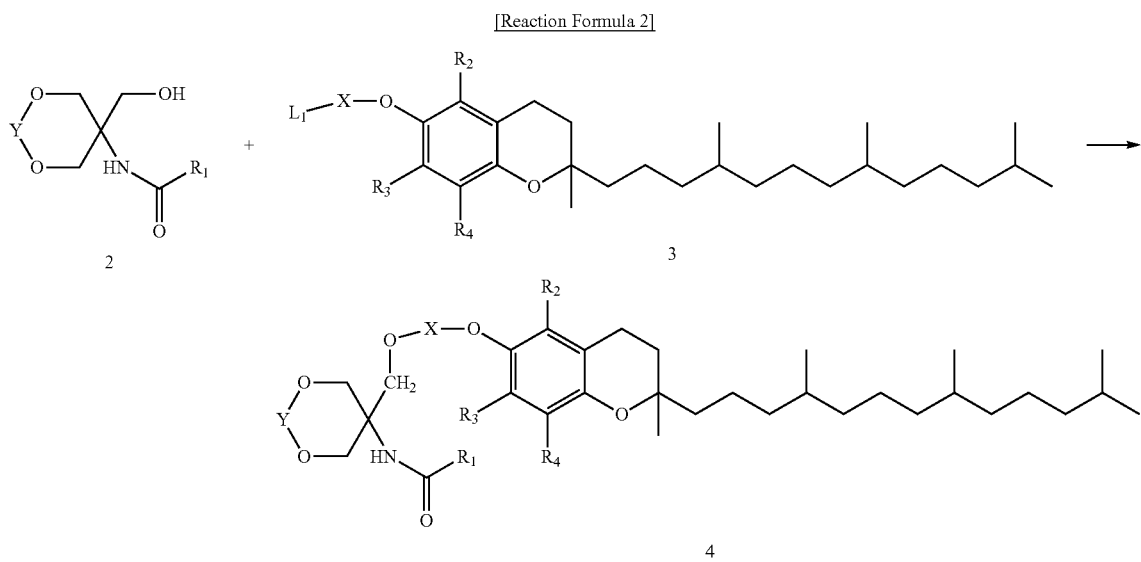

[Reaction Formula 2]

In Reaction Formula 2, $R_1$ to $R_4$, X, Y and $L_1$ have the same definitions as above.

As one example, this step may be carried out using a nucleophilic acyl substitution reaction or a nucleophilic substitution reaction. The nucleophilic acyl substitution reaction or the nucleophilic substitution reaction is not particularly limited in the present invention, and may be carried out for 0.5 hours to 72 hours and preferably for 1 hour to 12 hours in a range of 10° C. to 200° C. and preferably 10° C. to 100° C.

Herein, an organic solvent is preferred as the solvent used, and typically, one type selected from the group consisting of chloroform, dimethylformamide (DMF), methylene chloride (MC), diisopropyl ether, diethyl ether, tetrahydrofuran (THF), dimethylacetamide (DMA), dimethyl sulfoxide (DMSO), chlorobenzene, toluene, benzene, acetone and mixed solvents thereof may be used, and as one example, chloroform, methylene chloride or acetone is used.

The reaction may further include a base when necessary, and as one example, a base such as triethylamine, potassium carbonate or carbodiimide may be used.

The compound of Chemical Formula 2 and the compound of Chemical Formula 3, starting materials in this step, may be commercially purchased or directly prepared. In the present invention, these compounds are directly prepared and used as to describe later.

According to one embodiment of the present invention, the compound of Chemical Formula 2 may be prepared

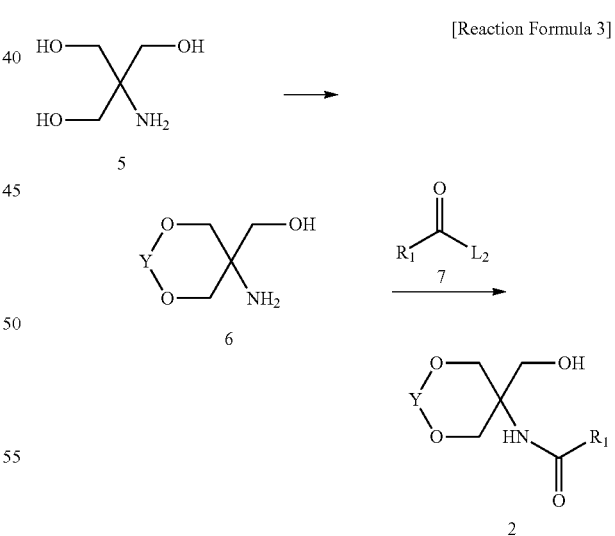

[Reaction Formula 3]

In Reaction Formula 3, $R_1$ and Y have the same definitions as above, and $L_2$ may be, for example, halogen, a C1 to C4 acyloxy group, a C1 to C4 alkyl carbonate group or a C1 to C4 alkoxy group as a leaving group.

The compound of Chemical Formula 5, the compound for introducing a protecting group to 1,3-diol of the compound of Chemical Formula 5, the compound of Chemical Formula 6 and the compound of Chemical Formula 7, which are reaction materials in Reaction Formula 2, may be purchased from various manufacturers including Aldrich, or may be directly prepared.

The 1,3-diol protecting group is not particularly limited in the present invention, and various protecting groups known in the art may be used. For example, a methylidene acetal, ethylidene acetal, isopropylidene ketal, cyclohexylidene ketal, benzylidene ketal or p-methoxybenzylidene acetal protecting group may be used. In one embodiment of the present invention, an isopropylidene ketal protecting group is introduced using dimethoxypropane.

Next, the fatty acid group-introduced compound of Chemical Formula 2 may be prepared by reacting the compound of Chemical Formula 6 prepared through introducing a protecting group with the compound of Chemical Formula 7 through an amide bond.

Preferably, the compound of Chemical Formula 7 is not particularly limited in the present invention, and any compound may be used as long as it satisfies the above-mentioned definition, and specific examples thereof may include palmitoyl chloride ($CH_3(CH_2)_{14}COCl$), myristoyl chloride ($CH_3(CH_2)_{12}COCl$) or stearoyl chloride ($CH_3(CH_2)_{16}COCl$).

Herein, the reaction condition, the temperature, the pressure, the time and the like of each reaction are not particularly limited in the present invention, and may be properly adjusted by those skilled in the art.

Meanwhile, the compound of Chemical Formula 3, another starting material, may be prepared including a step of reacting a compound of the following Chemical Formula 8 with a compound of Chemical Formula 9 or Chemical Formula 10.

[Chemical Formula 8]

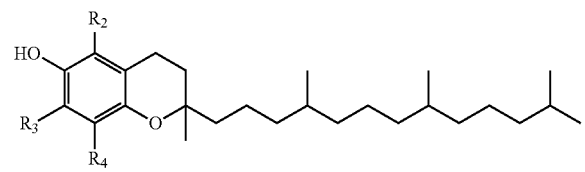

[Chemical Formula 9]

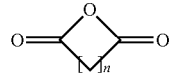

A-X-B     [Chemical Formula 10]

In Chemical Formulae 8 to 10, $R_2$ to $R_4$ and X are the same as described in Reaction Formula 1, n is 1 or 2, and A and B are the same as or different from each other, and each independently a hydroxyl group, halogen, a C1 to C4 acyloxy group, a C1 to C4 alkyl carbonate group or a C1 to C4 alkoxy group.

The compound of Chemical Formula 8 includes α-, β-, γ-, or δ-tocopherol, and derivatives derived therefrom, and may be purchased from various manufacturers including Aldrich, or may be directly prepared.

The compound of Chemical Formula 9 or Chemical Formula 10 is a compound for introducing

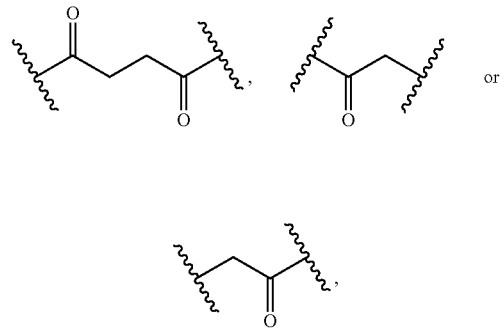 [SMILES: *C(=O)CCC(*)=O ; *CC(*)=O ; *CC(*)=O]

a linker, to Chemical Formula 8, and any compound may be used as long as it satisfies the above-mentioned definition.

As one example, the linker compound of Chemical Formula 9 may be succinic anhydride, and the linker compound of Chemical Formula 10 may be succinic acid, chloroacetyl chloride or ethyl bromoacetate, but are not limited thereto.

The compound of Chemical Formula 9 or Chemical Formula 10 may be commercially purchased or directly prepared.

Herein, the reaction condition, the temperature, the pressure, the time and the like are not particularly limited in the present invention, and may be properly adjusted by those skilled in the art.

(2) Preparation of Compound of Chemical Formula 1

Next, as shown in the following Reaction Formula 4, the compound of Chemical Formula 1 may be prepared by removing the protecting group from the compound of Chemical Formula 4:

[Reaction Formula 4]

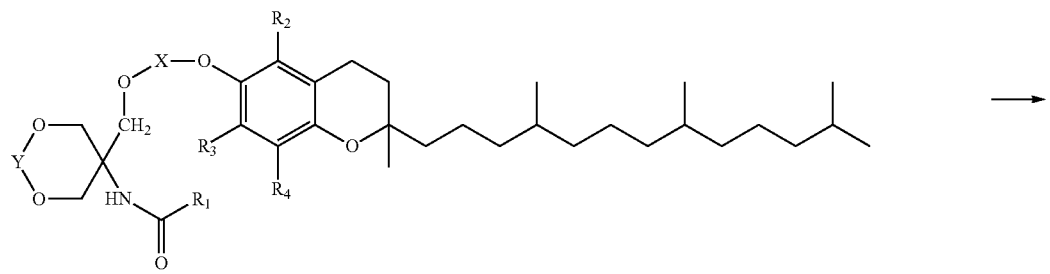

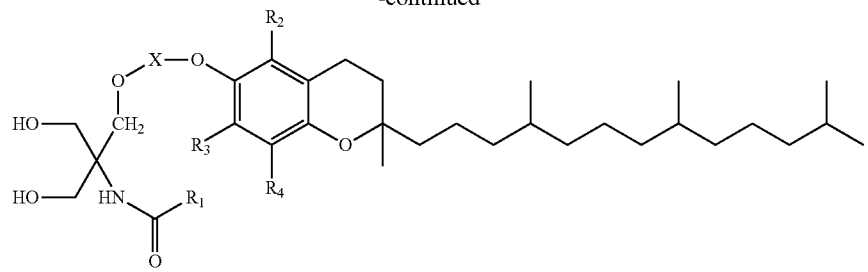

(in Reaction Formula 4, $R_1$ to $R_4$, X and Y are the same as described in Reaction Formula 1)

The reaction condition, the temperature, the pressure, the time and the like of the protecting group-removing reaction are not particularly limited, and may be properly adjusted depending on the used protecting group. As one example, the reaction may be carried out by acidic solution treatment or hydrogen gas addition under the presence of a metal catalyst, and according to one preferred embodiment of the present invention, may be carried out by acidic solution treatment.

As the acid used herein, hydrochloric acid, nitric acid, sulfuric acid or acetic used may be used, and as one example, hydrochloric acid may be used.

The condition of such a protecting group-removing reaction is not particularly limited in the present invention, and the reaction may be carried out for 0.5 hours to 72 hours and preferably from 1 hour to 12 hours in a range of −30° C. to 60° C. and preferably −30° C. to 40° C.

Herein, a polar solvent capable of dissolving acids may be used as the solvent, and one type selected from the group consisting of water, C1-C4 lower alcohols, tetrahydrofuran and mixed solvents thereof may be used. As one example, tetrahydrofuran may be used.

The compound of Chemical Formula 1 prepared using the above-described method is a material having excellent effects of restoring damaged skin and protecting skin from external stimuli, and may be used as an active material for restoring and preventing damaged skin. In addition, the compound of Chemical Formula 1 has an asymmetric molecular structure by including a tocopherol moiety, and therefore, improved properties such as enhanced solubility may be expected, and antioxidant effects may be provided when psuedoceramides are partially decomposed at an active site to release tocopherol.

The pseudo-ceramide compound of the present invention may be used in various fields, that is, various fields such as cosmetics, medicinal substances, external preparations and foods that natural ceramides, synthetic ceramides or pseudo-ceramides have been used in the art.

Advantageous Effects

A pseudo-ceramide compound of the present invention exhibits improved solubility compared to existing pseudo-ceramide compounds, and therefore, can be used as a substitute of natural ceramides, and is capable of providing antioxidant effects in addition to effects of strengthening and maintaining skin barrier function. The pseudo-ceramide compound of the present invention can be widely used in external preparations for skin, cosmetic compositions and the like.

BEST MODE

Hereinafter, the present invention will be described in more detail with reference to the following examples. However, the following examples are for illustrative purposes only, and the present invention is not limited to the following examples.

Example 1: Preparation of succinic acid 2-hexade-canoylamino-3-hydroxy-2-hydroxymethyl-propyl ester 2,5,7,8-tetramethyl-2-(4,8,12-trimethyl-tride-cyl)-chroman-6-yl Ester Compound A target compound of Chemical Formula 11 was prepared by the following Reaction Formula 5.

[Reaction Formula 5]

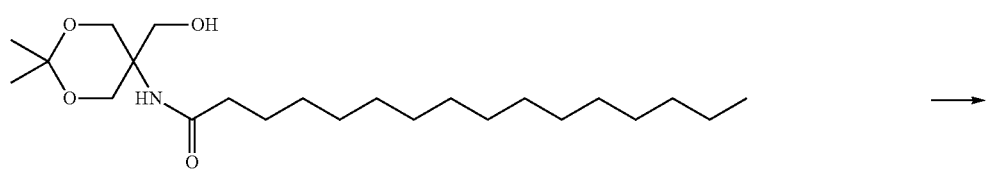

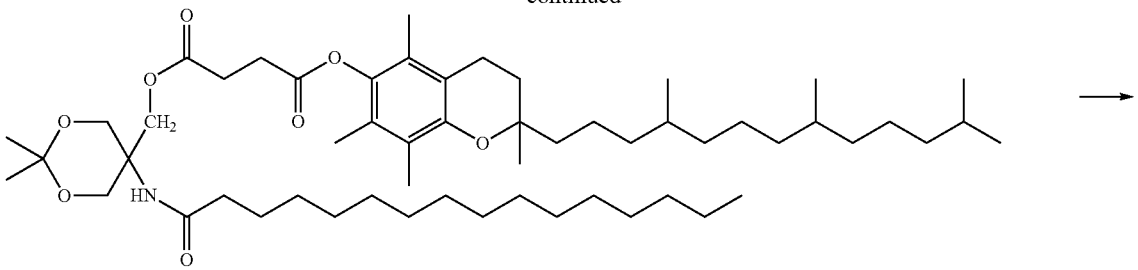

21

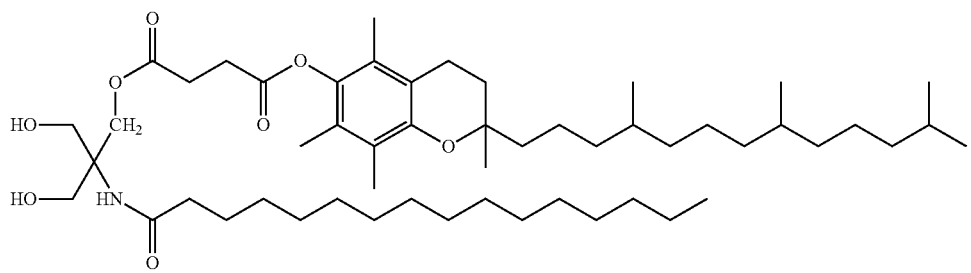

11

(1) Preparation of Compound of Chemical Formula 20

After dissolving (5-amino-2,2-dimethyl-[1,3]dioxan-5-yl)-methanol (1.61 g) synthesized using a method known in a literature (Helv. Chim. Acta 2003, 86, 2458~2470) with 2-amino-2-hydroxymethyl-propane-1,3-diol hydrochloride as a starting material in dichloromethane (50 mL) and adding triethylamine (1.7 mL) thereto, palmitoyl chloride (2.75 g) dissolved in dichloromethane (10 mL) was slowly added dropwise thereto while stirring at 0° C. The reaction solution was stirred for 3 hours at room temperature, and then washed with a dilute hydrochloric acid solution and a saturated sodium chloride solution. The organic solution layer was dried with anhydrous magnesium sulfate, filtered, vacuum concentrated and then recrystallized using dichloromethane and hexane to obtain 2.5 g of white solids of Chemical Formula 20.

$^1$H NMR (300 MHz, CDCl$_3$) δ 6.28 (brs, 1H), 5.18 (m, 1H), 3.83 (s, 4H), 3.65 (d, 2H, J=6.3 Hz), 2.28 (t, 2H, J=7.2 Hz), 1.65~1.25 (m, 32H), 0.88 (t, 3H, J=6.9 Hz).

(2) Preparation of Compound of Chemical Formula 21

After dissolving succinic acid mono-[2,5,7,8-tetramethyl-2-(4,8,12-trimethyl-tridecyl)-chroman-6-yl] ester (2.65 g) synthesized using a method known in a literature (Korean Patent No. 10-0352986) with (±)-α-tocopherol as a starting material in chloroform (20 mL) and adding triethylamine (0.8 mL) thereto, ethyl chloroformate (0.54 g) was added dropwise thereto, and the result was stirred for 30 minutes to prepare a mixed anhydride. The produced solids were filtered, and the filtrate including the mixed anhydride was used for the subsequent reaction.

After dissolving the compound of Chemical Formula 20 (2.0 g) obtained in the process (1) in chloroform (20 mL) and adding triethylamine (0.8 mL) thereto, the mixed anhydride filtrate obtained above was slowly added dropwise thereto, and the result was stirred for 2 hours at room temperature. The reaction solution was diluted with dichloromethane (100 mL), and washed with a dilute hydrochloric acid solution and a saturated sodium chloride solution. The organic solution layer was dried with anhydrous magnesium sulfate, filtered and vacuum distilled, and then a product was separated using column chromatography to obtain 2.2 g of a transparent liquid of Chemical Formula 21.

$^1$H NMR (300 MHz, CDCl$_3$) δ 5.76 (brs, 1H), 4.51 (s, 2H), 4.30 (m, 2H), 3.72 (m, 2H), 2.94 (m, 2H), 2.75 (m, 2H), 2.57 (m, 2H), 2.07 (m, 5H), 1.99 (s, 3H), 1.95 (s, 3H), 1.75~1.06 (m, 58H), 0.85 (m, 15H).

(3) Preparation of Compound of Chemical Formula 11

After dissolving the compound of Chemical Formula 21 (1.0 g) obtained in the process (2) in tetrahydrofuran (20 mL) and adding 3 N HCl (3 mL) thereto, the result was stirred at room temperature. After identifying that the starting material disappeared on TLC, the result was diluted with dichloromethane (50 mL), and then washed with a sodium bicarbonate solution and water. The organic layer was dried with anhydrous magnesium sulfate, filtered, vacuum distilled, and then separated using column chromatography to obtain 0.5 g of a compound of Chemical Formula 11.

$^1$H NMR (300 MHz, CDCl$_3$) δ 6.38 (brs, 1H), 4.30 (m, 3H), 3.69~3.43 (m, 5H), 2.97~2.55 (m, 6H), 2.32 (t, 2H, J=7.2 Hz), 2.07 (s, 3H), 1.99 (s, 3H), 1.95 (s, 3H), 1.80~1.14 (m, 52H), 0.85 (m, 15H).

Example 2: Preparation of succinic acid 3-hydroxy-2-hydroxymethyl-2-tetradecanoylamino-propyl ester 2,5,7,8-tetramethyl-2-(4,8,12-trimethyl-tridecyl)-chroman-6-yl ester Compound A target compound of Chemical Formula 12 was prepared by the following Reaction Formula 6.

[Reaction Formula 6]

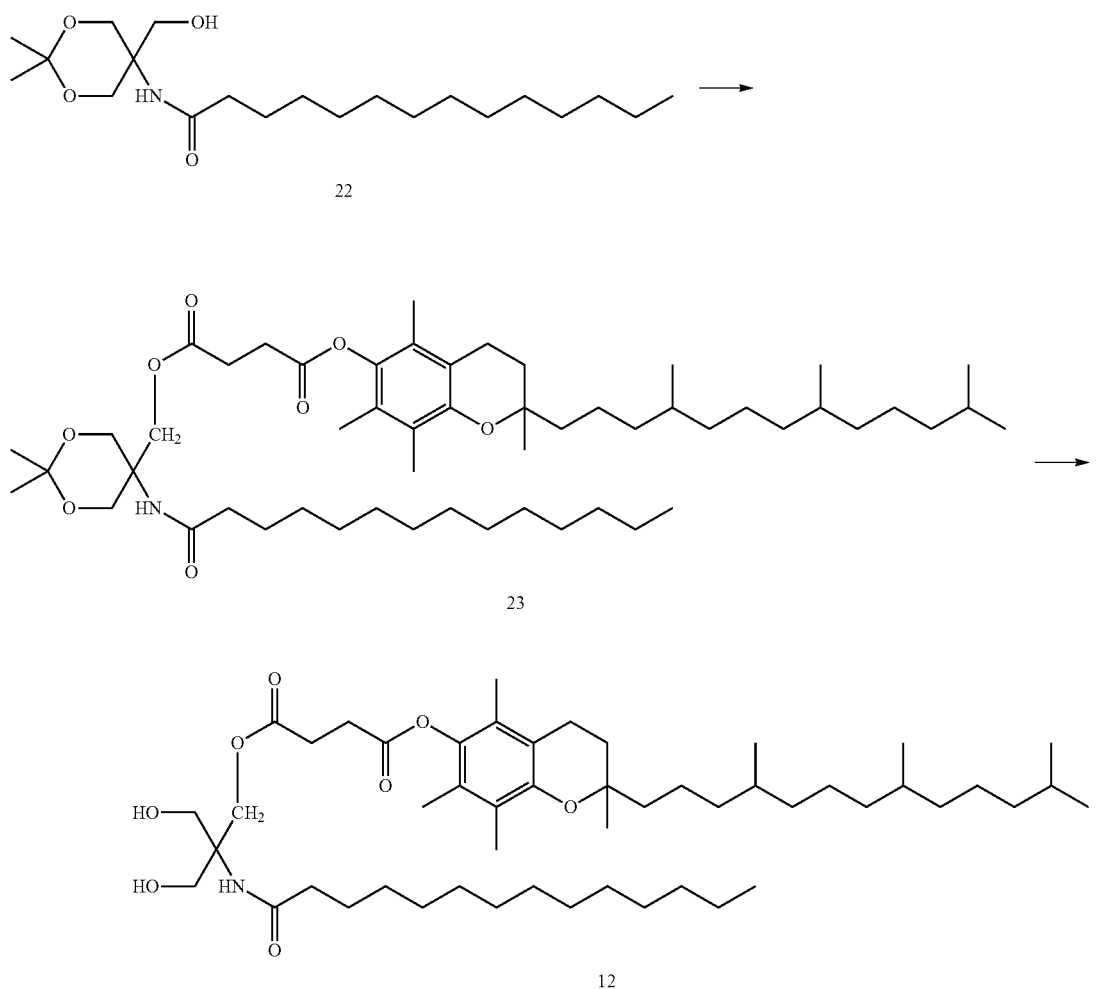

(1) Preparation of Compound of Chemical Formula 22

15 g of white solids of Chemical Formula 22 was obtained in the substantially same manner as in (1) of Example 1 except that (5-amino-2,2-dimethyl-[1,3]dioxa-5-yl)-methanol (12.8 g) was used as the starting material, and myristoyl chloride (19.5 g) was used instead of palmitoyl chloride (2.75 g).

$^1$H NMR (300 MHz, CDCl$_3$) δ 6.31 (brs, 1H), 5.20 (m, 1H), 3.85 (s, 4H), 3.67 (s, 2H), 2.31 (t, 2H, J=7.2 Hz), 1.68~1.28 (m, 28H), 0.90 (t, 3H, J=6.6 Hz).

(2) Preparation of Compound of Chemical Formula 23

After dissolving the compound of Chemical Formula 22 (3.72 g) obtained in the process (1) in dichloromethane (250 mL), succinic acid mono-[2,5,7,8-tetramethyl-2-(4,8,12-trimethyl-tridecyl)-chroman-6-yl]ester (5.3 g) and N-(3-dimethylaminopropyl)-N-ethylcarbodiimide hydrochloride (2.3 g) were consecutively added dropwise thereto, and the result was stirred for 12 hours at room temperature. The reaction solution was washed with water, and the organic solution layer was dried using anhydrous magnesium sulfate, filtered, vacuum concentrated and then separated using column chromatography to obtain 3.1 g of a compound of Chemical Formula 23.

$^1$H NMR (300 MHz, CDCl$_3$) δ 5.79 (brs, 1H), 4.53 (s, 2H), 4.32 (d, 2H, J=11.1 Hz), 3.74 (d, 2H, J=11.1 Hz), 2.96 (m, 2H), 2.77 (m, 2H), 2.58 (m, 2H), 2.08~2.05 (m, 5H), 2.00 (s, 3H), 1.96 (s, 3H), 1.79~1.15 (m, 54H), 0.87 (m, 15H).

(3) Preparation of Compound of Chemical Formula 12

1.3 g of a compound of Chemical Formula 12 was obtained in the substantially same manner as in (3) of Example 1 except that the compound of Chemical Formula 23 (2.5 g) was used instead of the compound of Chemical Formula 21.

$^1$H NMR (300 MHz, CDCl$_3$) δ 6.24 (brs, 1H), 4.34 (s, 2H), 4.23 (brs, 2H), 3.65 (m, 2H), 3.47 (m, 2H), 2.97 (m, 2H), 2.76 (m, 2H), 2.57 (m, 2H), 2.14~2.07 (m, 5H), 1.99 (s, 3H), 1.95 (s, 3H), 1.78~1.07 (m, 48H), 0.85 (m, 15H).

Example 3: Preparation of succinic acid 3-hydroxy-2-hydroxymethyl-2-octadecanoylamino-propyl ester 2,5,7,8-tetramethyl-2-(4,8,12-trimethyl-tridecyl)-chroman-6-yl Ester Compound A compound of Chemical Formula 13 was prepared by the following Reaction Formula 7.

[Reaction Formula 7]

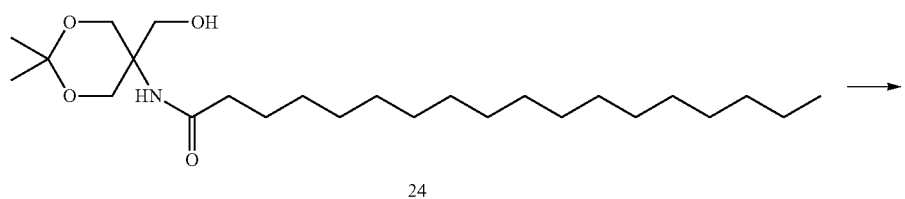

24

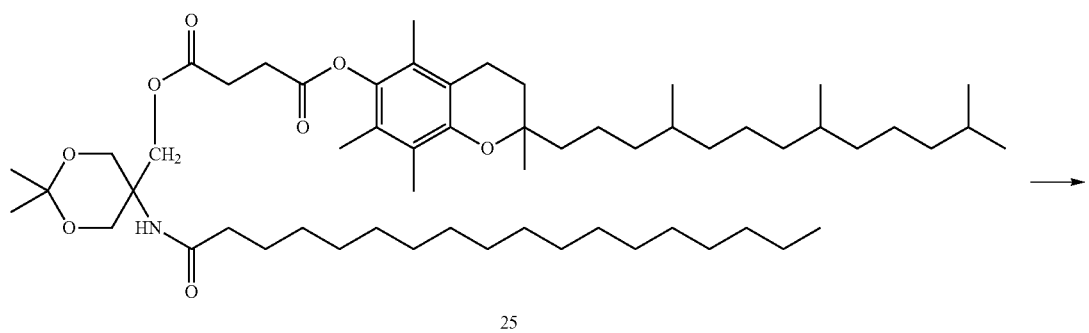

25

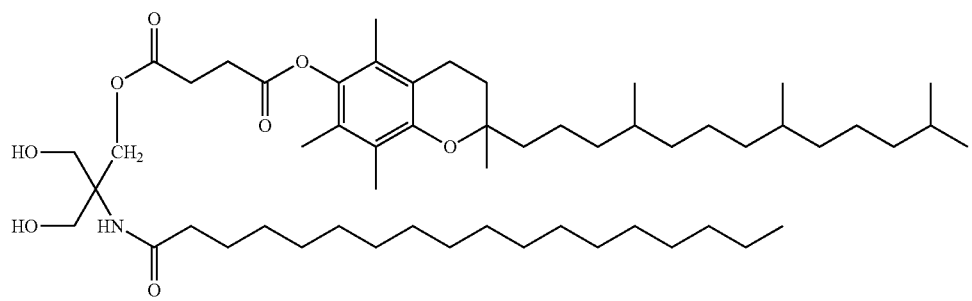

13

(1) Preparation of Compound of Chemical Formula 24

23 g of white solids of Chemical Formula 24 was obtained in the substantially same manner as in (1) of Example 1 except that (5-amino-2,2-dimethyl-[1,3]dioxa-5-yl)-methanol (12.8 g) was used as the starting material, and stearoyl chloride (24.5 g) was used instead of palmitoyl chloride (2.75 g).

$^1$H NMR (300 MHz, CDCl$_3$) δ 6.28 (brs, 1H), 5.17 (m, 1H), 3.83 (s, 4H), 3.64 (d, 2H, J=6.0 Hz), 2.28 (t, 2H, J=7.5 Hz), 1.65~1.25 (m, 36H), 0.87 (t, 3H, J=6.6 Hz).

(2) Preparation of Compound of Chemical Formula 25

2.0 g of a compound of Chemical Formula 25 was obtained in the substantially same manner as in (2) of Example 2 except that the compound of Chemical Formula 24 (4.27 g) obtained in the (1) was used instead of the compound of Chemical Formula 22.

$^1$H NMR (300 MHz, CDCl$_3$) δ 5.79 (brs, 1H), 4.53 (s, 2H), 4.32 (d, 2H, J=11.7 Hz), 3.74 (d, 2H, J=11.7 Hz), 2.96 (m, 2H), 2.77 (m, 2H), 2.59 (m, 2H), 2.09~2.04 (m, 5H), 2.01 (s, 3H), 1.97 (s, 3H), 1.87~1.15 (m, 62H), 0.86 (m, 15H).

(3) Preparation of Compound of Chemical Formula 13

0.75 g of a compound of Chemical Formula 13 was obtained in the substantially same manner as in (3) of Example 1 except that the compound of Chemical Formula 25 (1.66 g) was used instead of the compound of Chemical Formula 21.

$^1$H NMR (300 MHz, CDCl$_3$) δ 6.25 (brs, 1H), 4.34 (s, 2H), 4.24 (brs, 2H), 3.65 (m, 2H), 3.45 (m, 2H), 2.97 (m, 2H), 2.76 (m, 2H), 2.57 (m, 2H), 2.14~2.07 (m, 5H), 1.99 (s, 3H), 1.95 (s, 3H), 1.78~1.24 (m, 56H), 0.86 (m, 15H).

Example 4: Preparation of (2-hexadecanoylamino-3-hydroxy-2-hydroxymethyl-propoxy)-acetic acid 2,5,7,8-tetramethyl-2-(4,8,12-trimethyl-tridecyl)-chroman-6-yl Ester Compound A target compound of Chemical Formula 14 was prepared by the following Reaction Formula 8.

[Reaction Formula 8]

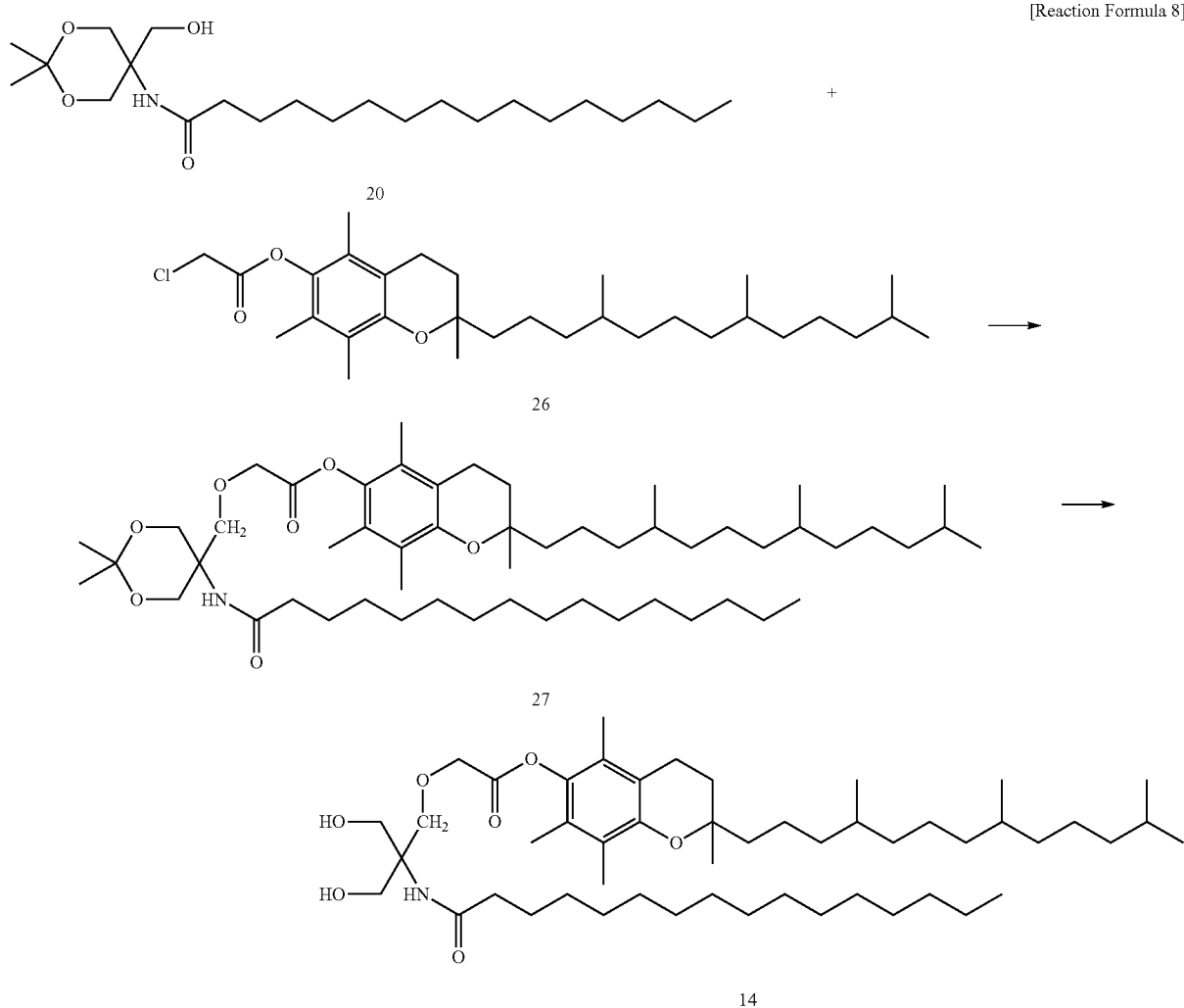

(1) Preparation of Compound of Chemical Formula 26

After dissolving (±)-α-tocopherol (5 g) in toluene (20 mL) and adding pyridine (1 mL) thereto, chloroacetyl chloride (1 mL) dissolved in toluene (20 mL) was slowly added dropwise to this solution. The result was stirred for 30 minutes at room temperature, then produced solids were filtered and removed, and then the organic layer was washed with a saturated aqueous sodium chloride solution, and dried with anhydrous magnesium sulfate, filtered, vacuum concentrated and then separated using column chromatography to obtain 4.65 g of a compound of Chemical Formula 26.

$^1$H NMR (300 MHz, CDCl$_3$) δ 4.32 (s, 2H), 2.59 (t, 2H, J=6.6 Hz), 2.09 (s, 3H), 2.03 (s, 3H), 1.98 (s, 3H), 1.87~1.11 (m, 26H), 0.83 (m, 12H).

(2) Preparation of Compound of Chemical Formula 27

After dissolving the compound of Chemical Formula 26 (1 g) obtained in (1) and the compound of Chemical Formula 20 (0.8 g) obtained in (1) of Example 1 in acetone (50 mL), potassium carbonate (1.32 g) powder was added thereto, and the result was heated under reflux for 12 hours. After the reaction, the reaction solution was filtered and concentrated, then diluted with dichloromethane, and washed with dilute hydrochloric acid and a saturated aqueous sodium chloride solution. The organic solution was dried with anhydrous magnesium sulfate, filtered, vacuum concentrated and then separated using column chromatography to obtain 0.27 g of a compound of Chemical Formula 27.

$^1$H NMR (300 MHz, CDCl$_3$) δ 5.78 (brs, 1H), 4.62 (s, 2H), 4.31 (s, 2H), 4.28 (d, 2H, J=11.7 Hz), 3.80 (d, 2H, J=11.7 Hz), 2.56 (t, 2H, J=6.6 Hz), 2.18~2.17 (m, 5H), 2.13 (s, 3H), 2.07 (s, 3H), 1.83~1.07 (m, 58H), 0.85 (m, 15H).

(3) Preparation of Compound of Chemical Formula 14

0.1 g of a compound of Chemical Formula 14 was obtained in the substantially same manner as in (3) of Example 1 except that the compound of Chemical Formula 27 (0.2 g) obtained in the (2) was used instead of the compound of Chemical Formula 21.

$^1$H NMR (300 MHz, CDCl$_3$) δ 6.41 (brs, 1H), 4.48 (s, 2H), 4.32 (s, 2H), 4.22 (brs, 2H), 3.66 (m, 2H), 3.51 (m, 2H), 2.54 (m, 2H), 2.21 (m, 2H), 2.14 (s, 3H), 2.10 (s, 3H), 2.05 (s, 3H), 1.75~1.12 (m, 52H), 0.84 (m, 15H).

Example 5: Preparation of (3-hydroxy-2-hydroxymethyl-2-tetradecanoylamino-propoxy)-acetic acid 2,5,7,8-tetramethyl-2-(4,8,12-trimethyl-tridecyl)-chroman-6-yl Ester Compound A target compound of Chemical Formula 15 was prepared by the following Reaction Formula 9.

[Reaction Formula 9]

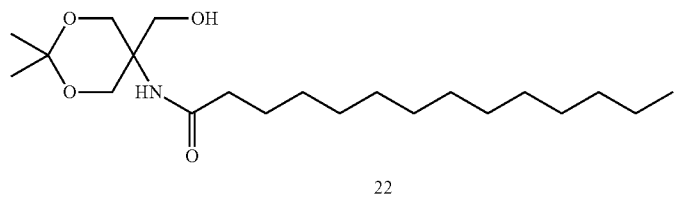

22

+

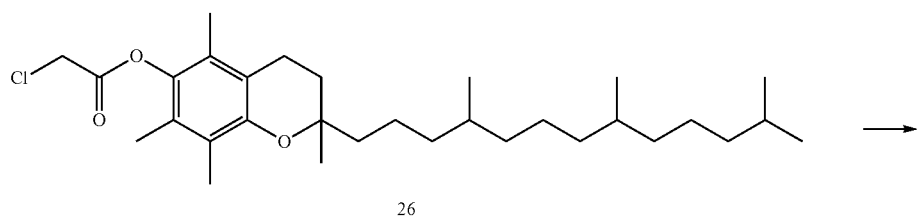

26

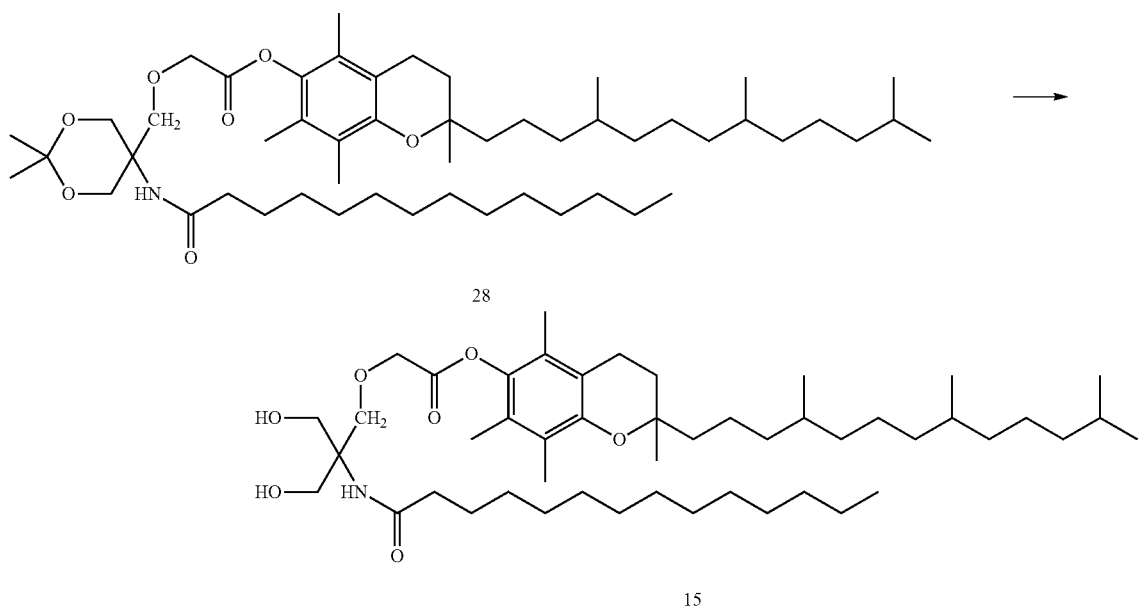

28

15

(1) Preparation of Compound of Chemical Formula 28

1.4 g of a compound of Chemical Formula 28 was obtained in the substantially same manner as in (2) of Example 4 except that the compound of Chemical Formula 22 (2.54 g) obtained in (1) of Example 2 was used instead of the compound of Chemical Formula 20.

$^1$H NMR (300 MHz, CDCl$_3$) δ 5.78 (brs, 1H), 4.62 (s, 2H), 4.34~4.26 (m, 4H), 3.80 (d, 2H, J=12.0 Hz), 2.55 (t, 2H, J=6.6 Hz), 2.18~2.16 (m, 5H), 2.12 (s, 3H), 2.06 (s, 3H), 1.85~1.07 (m, 54H), 0.85 (m, 15H).

(2) Preparation of Compound of Chemical Formula 15

0.1 g of a compound of Chemical Formula 15 was obtained in the substantially same manner as in (3) of Example 1 except that 0.34 g of the compound of Chemical Formula 28 obtained in the (1) was used instead of the compound of Chemical Formula 21.

$^1$H NMR (300 MHz, CDCl$_3$) δ 6.45 (brs, 1H), 4.49 (s, 2H), 4.33~4.29 (m, 4H), 3.69 (m, 2H), 3.53 (m, 2H), 2.56 (m, 2H), 2.23 (m, 2H), 2.16 (s, 3H), 2.12 (s, 3H), 2.07 (s, 3H), 1.81~1.22 (m, 48H), 0.85 (m, 15H)

Example 6: Preparation of (3-hydroxy-2-hydroxymethyl-2-octadecanoylamino-propoxy)-acetic acid 2,5,7,8-tetramethyl-2-(4,8,12-trimethyl-tridecyl)-chroman-6-yl Ester Compound A target compound of Chemical Formula 16 was prepared by the following Reaction Formula 10.

[Reaction Formula 10]

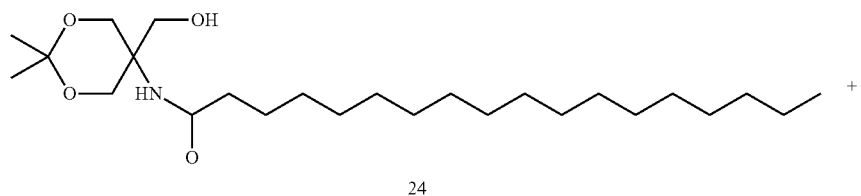

24

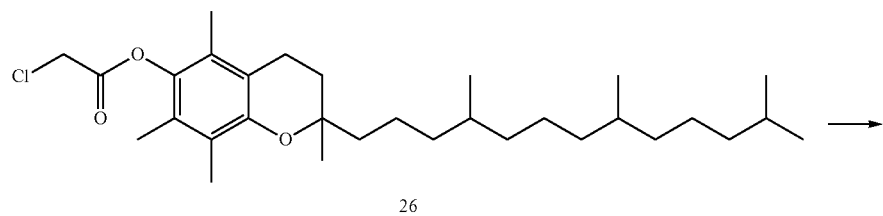

26

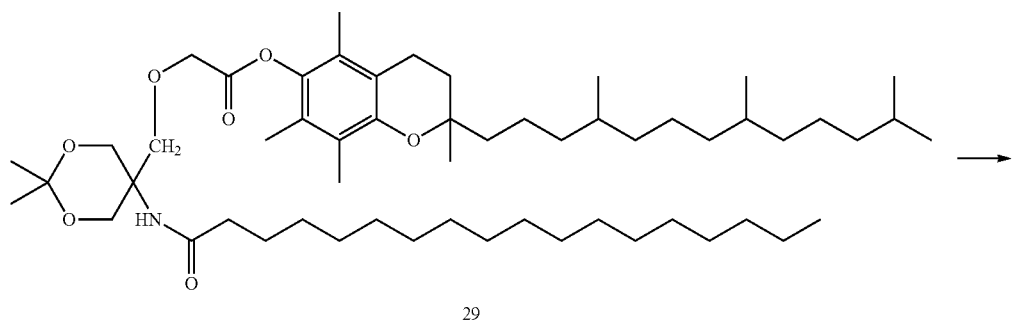

29

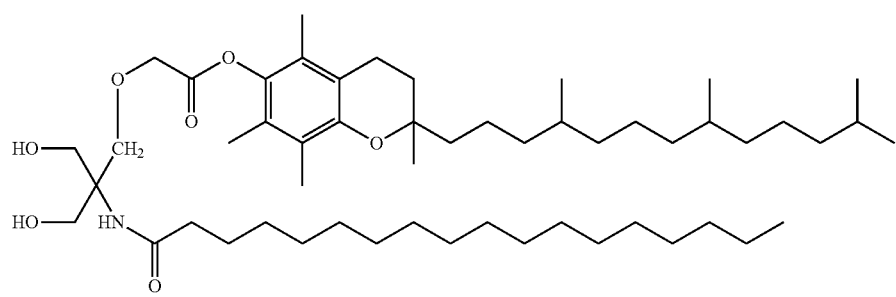

16

(1) Preparation of Compound of Chemical Formula 29

1.22 g of a compound of Chemical Formula 29 was obtained in the substantially same manner as in (2) of Example 4 except that the compound of Chemical Formula 24 (2.13 g) obtained in (1) of Example 3 was used instead of the compound of Chemical Formula 20.

$^1$H NMR (300 MHz, CDCl$_3$) δ 5.78 (brs, 1H), 4.61 (s, 2H), 4.31~4.25 (m, 4H), 3.80 (d, 2H, J=11.7 Hz), 2.55 (m, 2H), 2.16~2.12 (m, 8H), 2.06 (s, 3H), 1.76~1.23 (m, 62H), 0.85 (m, 15H).

(2) Preparation of Compound of Chemical Formula 16

0.35 g of a compound of Chemical Formula 16 was obtained in the substantially same manner as in (3) of Example 1 except that the compound of Chemical Formula 29 (1 g) obtained in the (1) was used instead of the compound of Chemical Formula 21.

$^1$H NMR (300 MHz, CDCl$_3$) δ 6.43 (brs, 1H), 4.50 (s, 2H), 4.34~4.16 (m, 4H), 3.68 (m, 2H), 3.53 (m, 2H), 2.56 (m, 2H), 2.21 (m, 2H), 2.16 (s, 3H), 2.12 (s, 3H), 2.07 (s, 3H), 1.81~1.14 (m, 56H), 0.85 (m, 15H).

Example 7: Preparation of [2,5,7,8-tetramethyl-2-(4, 8,12-trimethyl-tridecyl)-chroman-6-yloxy]-acetic acid 2-hexadecanoylamino-3-hydroxy-2-hydroxymethyl-propyl Ester Compound A target compound of Chemical Formula 17 was prepared by the following Reaction Formula 11.

[Reaction Formula 11]

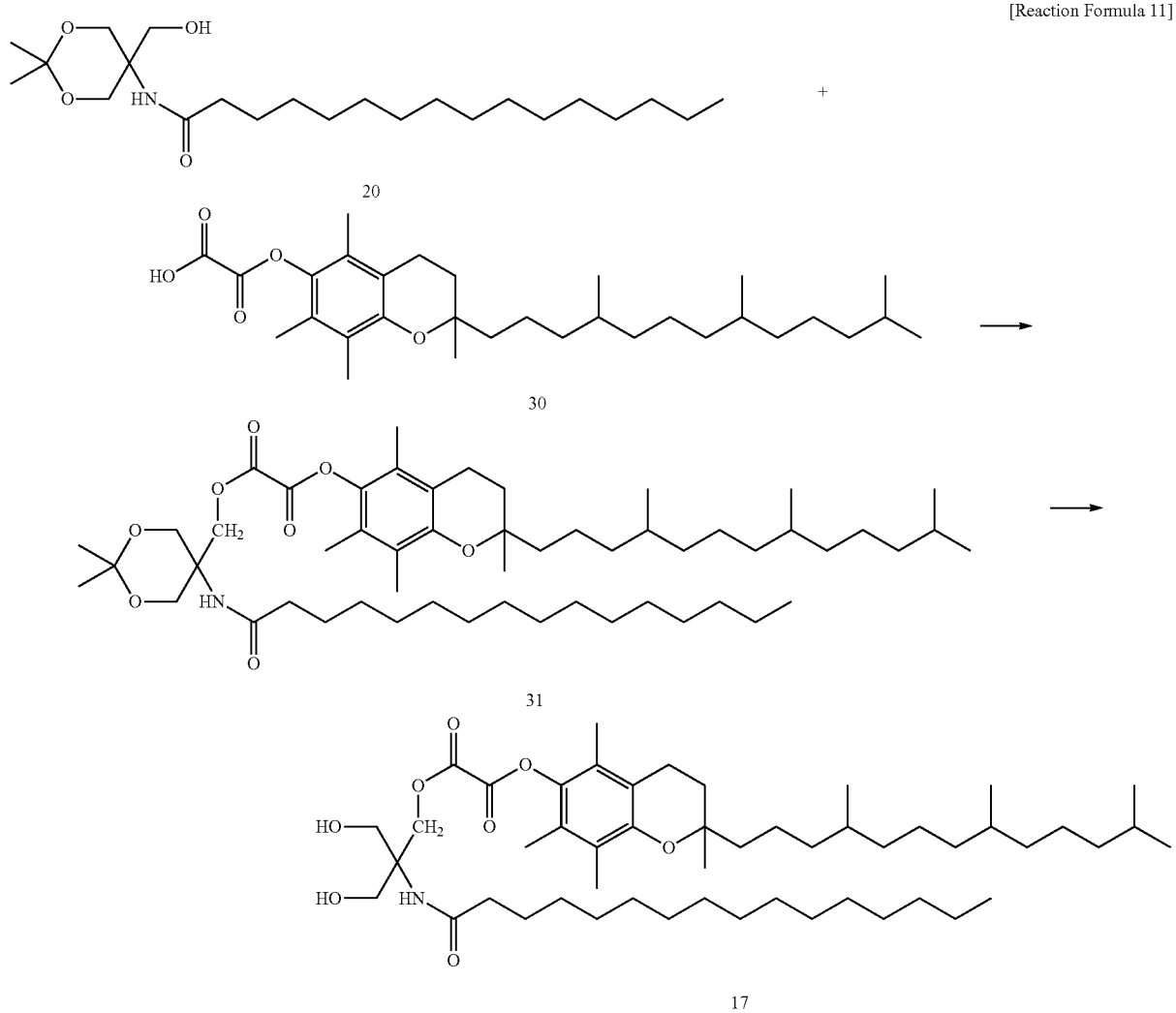

(1) Preparation of Compound of Chemical Formula 30

After dissolving 20 g of (±)-α-tocopherol in N,N'-dimethylformamide (400 mL) and adding ethyl bromoacetate (11 g) thereto, the result was stirred while adding powder state potassium hydroxide (13.5 g) thereto in small installments thereto with the temperature of the reaction solution kept at 0° C. After stirring the result for 24 hours at room temperature, the reaction was stopped using a 5 N aqueous hydrochloric acid solution. The layers were separated by adding ethyl acetate thereto, and the result was washed with water and a saturated aqueous sodium chloride solution. The organic layer was dried with anhydrous magnesium sulfate, filtered, vacuum concentrated, and then separated using column chromatography to obtain 14.7 g of a compound of Chemical Formula 30.

$^1$H NMR (300 MHz, CDCl$_3$) δ 4.33 (s, 2H), 2.57 (t, 2H, J=6.6 Hz), 2.16 (s, 3H), 2.12 (s, 3H), 2.08 (s, 3H), 1.78 (m, 2H), 1.56~1.07 (m, 24H), 0.85 (m, 12H).

(2) Preparation of Compound of Chemical Formula 31

After dissolving the compound of Chemical Formula 30 (4 g) obtained in the (1) in chloroform (100 mL), SOCl$_2$ (1.45 mL) was added thereto, and the result was heated under reflux for 1 hour. The reaction solution was cooled to room temperature, and then vacuum concentrated to produce [2,5,7,8-tetramethyl-2-(4,8,12-trimethyl-tridecyl)-chroman-6-yloxy]-acetic acid chloride, which was used in the subsequent reaction without purification.

After dissolving 2.8 g of the compound of Chemical Formula 20 obtained in (1) of Example 1 in dichloromethane (50 mL) and adding trimethylamine (1.53 mL) thereto, [2,5,7,8-tetramethyl-2-(4,8,12-trimethyl-tridecyl)-chroman-6-yloxy]-acetic acid chloride dissolved in dichloromethane (50 mL) was added dropwise thereto. The result was stirred for 3 hours at room temperature, then the reaction solution was washed with water and a saturated aqueous sodium chloride solution, and then the organic layer was dried with anhydrous magnesium sulfate, filtered, vacuum concentrated, and then separated using column chromatography to obtain 3.3 g of a compound of Chemical Formula 31.

$^1$H NMR (300 MHz, CDCl$_3$) δ 5.79 (brs, 1H), 4.62 (s, 2H), 4.31~4.26 (m, 4H), 3.80 (d, 2H, J=11.4 Hz), 2.56 (m, 2H), 2.18~2.17 (m, 5H), 2.13 (s, 3H), 2.07 (s, 3H), 1.79~1.08 (m, 58H), 0.85 (m, 15H).

(3) Preparation of Compound of Chemical Formula 17

0.23 g of a compound of Chemical Formula 17 was obtained in the substantially same manner as in (3) of Example 1 except that the compound of Chemical Formula 31 (1 g) obtained in the (2) was used instead of the compound of Chemical Formula 21.

$^1$H NMR (300 MHz, CDCl$_3$) δ 6.42 (brs, 1H), 4.50 (s, 2H), 4.34 (s, 2H), 4.21 (m, 2H), 3.70 (m, 2H), 3.53 (m, 2H), 2.56 (t, 2H, J=6.6 Hz), 2.24 (m, 2H), 2.16 (s, 3H), 2.12 (s, 3H), 2.07 (s, 3H), 1.81~1.07 (m, 52H), 0.84 (m, 15H).

Example 8: Preparation of [2,5,7,8-tetramethyl-2-(4,8,12-trimethyl-tridecyl)-chroman-6-yloxy]-acetic acid 3-hydroxy-2-hydroxymethyl-2-tetradecanoylamino-propyl Ester Compound A target compound of Chemical Formula 18 was prepared by the following Reaction Formula 12.

2H), 2.19~2.17 (m, 5H), 2.13 (s, 3H), 2.07 (s, 3H), 1.79~1.46 (m, 54H), 0.85 (m, 15H).

(2) Preparation of Compound of Chemical Formula 18

0.45 g of a compound of Chemical Formula 18 was obtained in the substantially same manner as in (3) of Example 1 except that the compound of Chemical Formula 32 (1 g) obtained in the (1) was used instead of the compound of Chemical Formula 21.

$^1$H NMR (300 MHz, CDCl$_3$) δ 6.45 (brs, 1H), 4.51 (s, 2H), 4.35~4.30 (m, 4H), 3.70 (m, 2H), 3.53 (m, 2H), 2.57 (m, 2H), 2.25 (m, 2H), 2.17 (s, 3H), 2.13 (s, 3H), 2.08 (s, 3H), 1.82~1.15 (m, 48H), 0.86 (m, 15H).

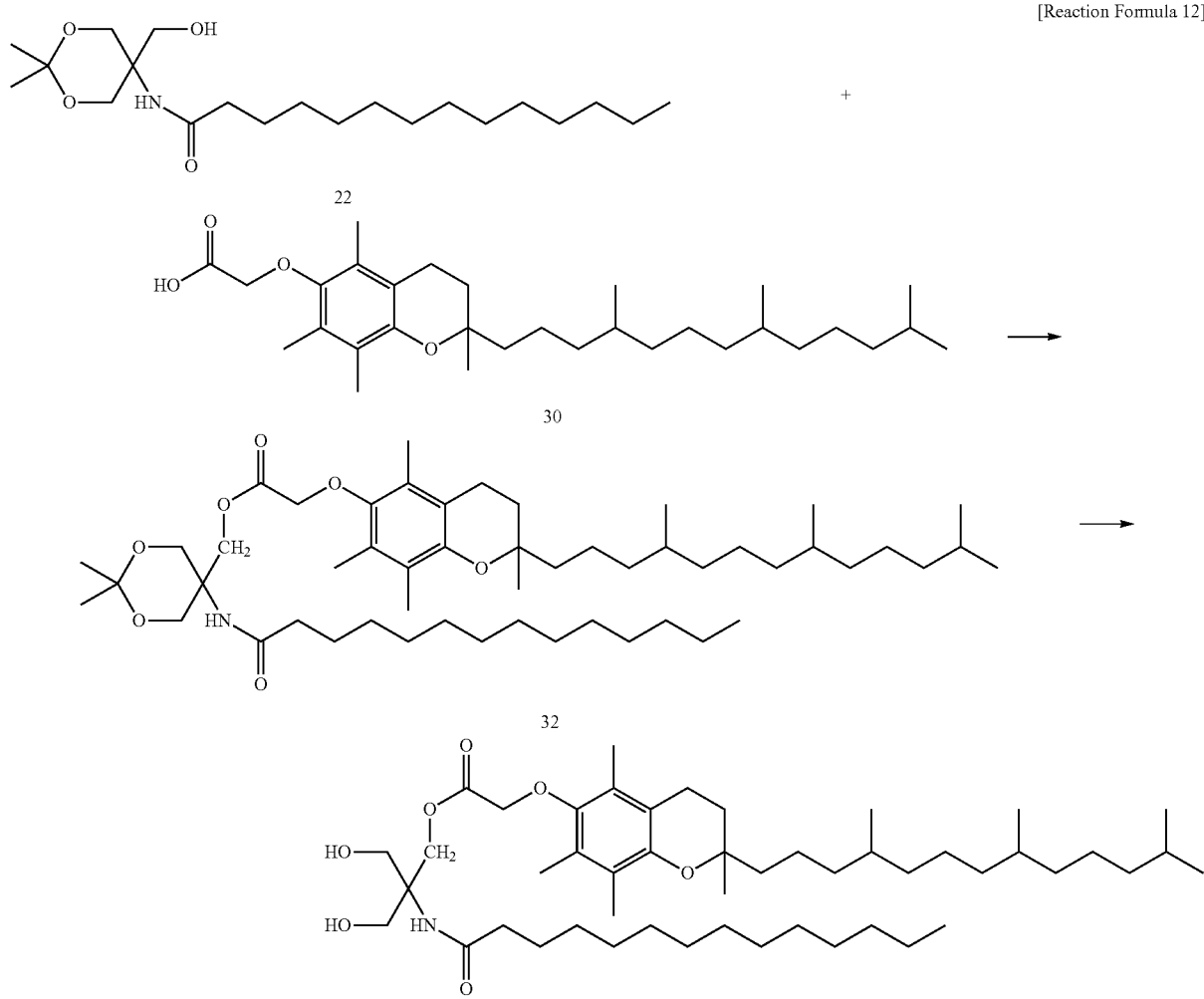

[Reaction Formula 12]

(1) Preparation of Compound of Chemical Formula 32

3.41 g of a compound of Chemical Formula 32 was obtained in the substantially same manner as in (2) of Example 7 except that the compound of Chemical Formula 22 (2.97 g) obtained in (1) of Example 2 was used instead of the compound of Chemical Formula 20.

$^1$H NMR (300 MHz, CDCl$_3$) δ 5.78 (brs, 1H), 4.62 (s, 2H), 4.32~4.19 (m, 4H), 3.80 (d, 2H, J=12.0 Hz), 2.56 (m, Example 9: Preparation of [2,5,7,8-tetramethyl-2-(4,8,12-trimethyl-tridecyl)-chroman-6-yloxy]-acetic acid 3-hydroxy-2-hydroxymethyl-2-octadecanoylamino-propyl Ester Compound A target compound of Chemical Formula 19 was prepared by the following Reaction Formula 13.

[Reaction Formula 13]

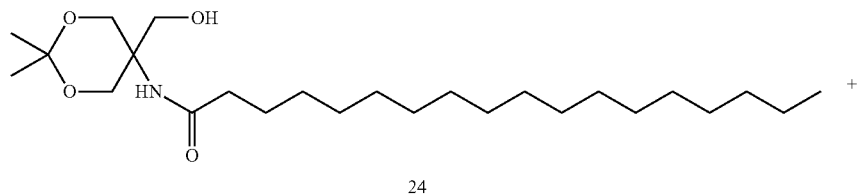

24

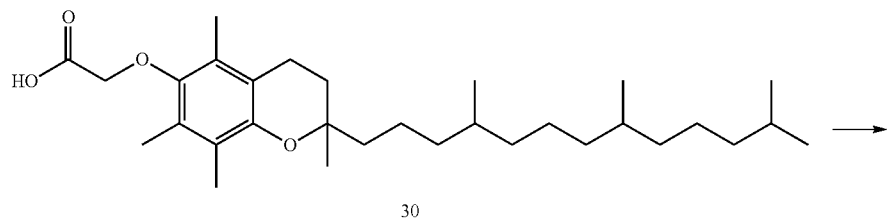

30

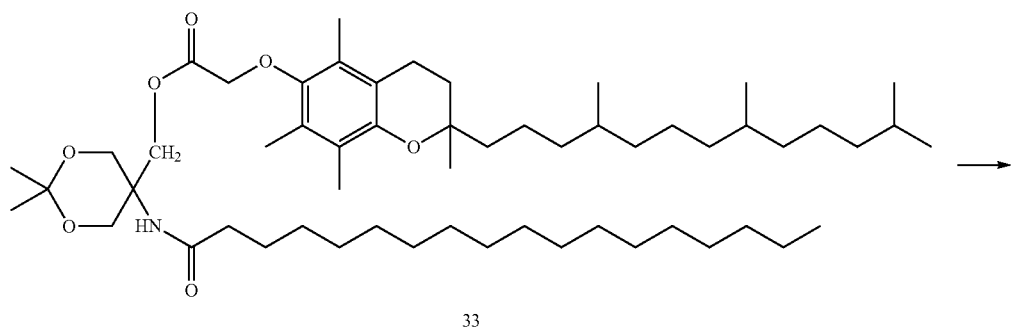

33

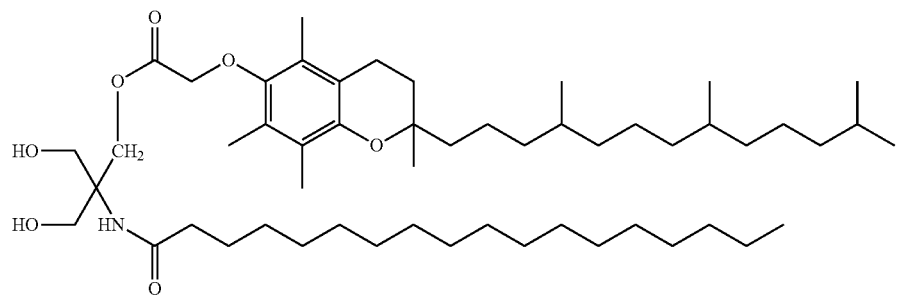

19

(1) Preparation of Compound of Chemical Formula 33

3.22 g of a compound of Chemical Formula 33 was obtained in the substantially same manner as in (2) of Example 7 except that the compound of Chemical Formula 24 (3.42 g) obtained in (1) of Example 3 was used instead of the compound of Chemical Formula 20.

$^1$H NMR (300 MHz, CDCl$_3$) δ 5.78 (brs, 1H), 4.61 (s, 2H), 4.31~4.26 (m, 4H), 3.80 (d, 2H, J=11.7 Hz), 2.55 (m, 2H), 2.16 (m, 5H), 2.13 (s, 3H), 2.07 (s, 3H), 1.81~1.07 (m, 62H), 0.85 (m, 15H).

(2) Preparation of Compound of Chemical Formula 19

0.38 g of a compound of Chemical Formula 19 was obtained in the substantially same manner as in (3) of Example 1 except that the compound of Chemical Formula 33 (1 g) obtained in the (1) was used instead of the compound of Chemical Formula 21.

$^1$H NMR (300 MHz, CDCl$_3$) δ 6.45 (brs, 1H), 4.51 (s, 2H), 4.35~4.25 (m, 4H), 3.72 (m, 2H), 3.54 (m, 2H), 2.57 (m, 2H), 2.25 (m, 2H), 2.18 (s, 3H), 2.14 (s, 3H), 2.08 (s, 3H), 1.83~1.15 (m, 56H), 0.86 (m, 15H).

The invention claimed is:

1. A pseudo-ceramide compound represented by the following Chemical Formula 1:

[Chemical Formula 1]

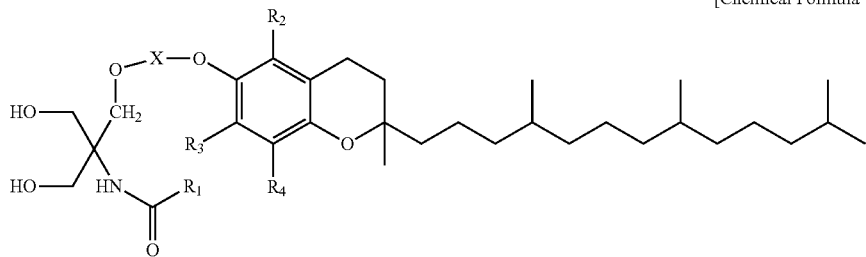

wherein R₁ is a C9 to C23 saturated or unsaturated aliphatic hydrocarbon group unsubstituted or substituted with a hydroxyl group;
R₂, R₃ and R₄ are the same as or different from each other, and each independently hydrogen or a C1 to C4 alkyl group; and
X is

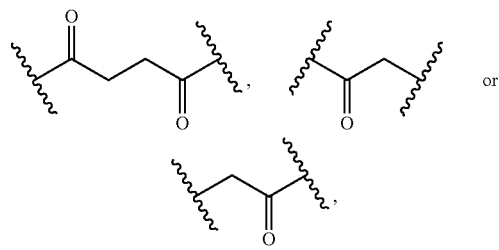

or

2. The pseudo-ceramide compound according to claim 1, wherein R₁ is a C13 to C17 saturated or unsaturated aliphatic hydrocarbon group, and R₂, R₃ and R₄ are hydrogen or a methyl group.

3. The pseudo-ceramide compound according to claim 1, wherein the pseudo-ceramide compound is succinic acid 2-hexadecanoylamino-3-hydroxy-2-hydroxymethyl-propyl ester 2,5,7,8-tetramethyl-2-(4,8,12-trimethyl-tridecyl)-chroman-6-yl ester, succinic acid 3-hydroxy-2-hydroxymethyl-2-tetradecanoylamino-propyl ester 2,5,7,8-tetramethyl-2-(4,8,12-trimethyl-tridecyl)-chroman-6-yl ester, succinic acid 3-hydroxy-2-hydroxymethyl-2-octadecanoylamino-propyl ester 2,5,7,8-tetramethyl-2-(4,8,12-trimethyl-tridecyl)-chroman-6-yl ester, (2-hexadecanoylamino-3-hydroxy-2-hydroxymethyl-propoxy)-acetic acid 2,5,7,8-tetramethyl-2-(4,8,12-trimethyl-tridecyl)-chroman-6-yl ester, (3-hydroxy-2-hydroxymethyl-2-tetradecanoylamino-propoxy)-acetic acid 2,5,7,8-tetramethyl-2-(4,8,12-trimethyl-tridecyl)-chroman-6-yl ester, (3-hydroxy-2-hydroxymethyl-2-octadecanoylamino-propoxy)-acetic acid 2,5,7,8-tetramethyl-2-(4,8,12-trimethyl-tridecyl)-chroman-6-yl ester, [2,5,7,8-tetramethyl-2-(4,8,12-trimethyl-tridecyl)-chroman-6-yloxy]-acetic acid 2-hexadecanoylamino-3-hydroxy-2-hydroxymethyl-propyl ester, [2,5,7,8-tetramethyl-2-(4,8,12-trimethyl-tridecyl)-chroman-6-yloxy]-acetic acid 3-hydroxy-2-hydroxymethyl-2-tetradecanoylamino-propyl ester, or [2,5,7,8-tetramethyl-2-(4,8,12-trimethyl-tridecyl)-chroman-6-yloxy]-acetic acid 3-hydroxy-2-hydroxymethyl-2-octadecanoylamino-propyl ester.

4. A method for preparing the pseudo-ceramide compound of claim 1, the method comprising:
obtaining a compound of Chemical Formula 4 by reacting a compound of Chemical Formula 2 with a compound of Chemical Formula 3; and
obtaining the compound of Chemical Formula 1 by deprotecting the compound of Chemical Formula 4:

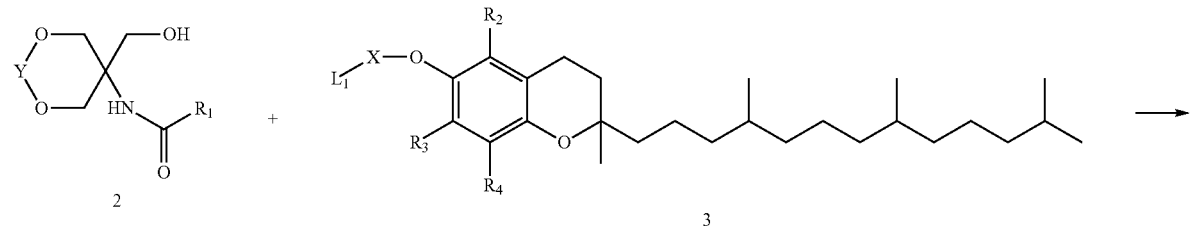

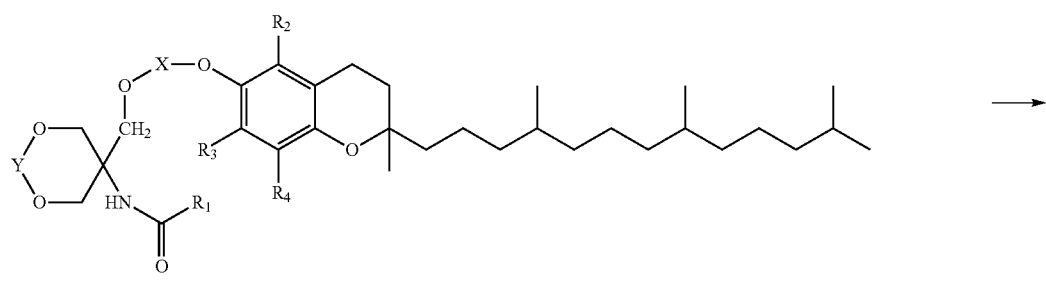

-continued

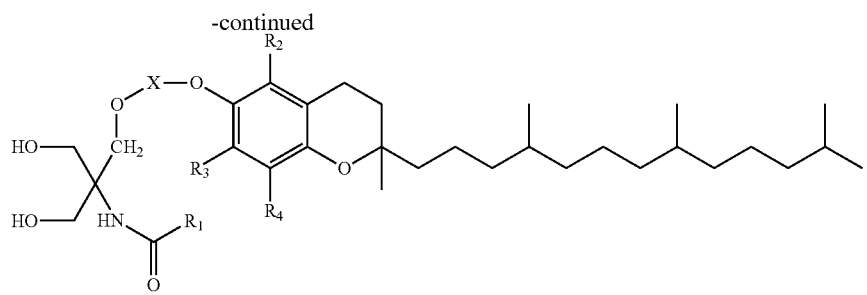

1 wherein R₁ is a C9 to C23 saturated or unsaturated aliphatic hydrocarbon group unsubstituted or substituted with a hydroxyl group;

R₂, R₃ and R₄ are the same as or different from each other, and each independently hydrogen or a C1 to C4 alkyl group;

X is

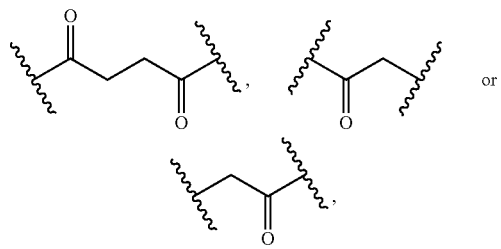

Y is alkylidene, ethylidene, isopropylidene, cyclohexylidene, benzylidene or p-methoxybenzylidene; and L₁ is a hydroxyl group, halogen, a C1 to C4 acyloxy group, a C1 to C4 alkyl carbonate group or a C1 to C4 alkoxy group.

5. The method for preparing the pseudo-ceramide compound according to claim 4, wherein R₁ is a C13 to C17 saturated or unsaturated aliphatic hydrocarbon group, and R₂, R₃ and R₄ are hydrogen or a methyl group.

6. The method for preparing the pseudo-ceramide compound according to claim 4, further comprising:
obtaining a compound of Chemical Formula 6 by introducing a protecting group to a compound of Chemical Formula 5; and
obtaining the compound of Chemical Formula 2 by reacting the compound of Chemical Formula 6 with a compound of Chemical Formula 7:

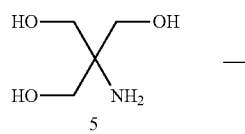

5

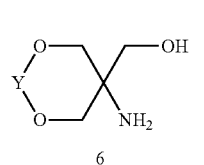

6

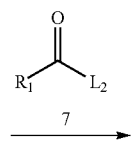

7

-continued

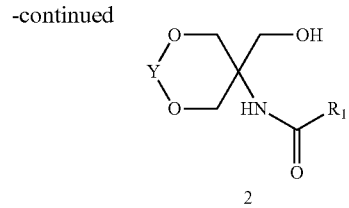

2 wherein R₁ and Y have the same definitions as in claim 4, L₂ is halogen, a C1 to C4 acyloxy group, a C1 to C4 alkyl carbonate group or a C1 to C4 alkoxy group.

7. The method for preparing the pseudo-ceramide compound according to claim 6, wherein the compound of Chemical Formula 7 is palmitoyl chloride ($CH_3(CH_2)_{14}COCl$), myristoyl chloride ($CH_3(CH_2)_{12}COCl$) or stearoyl chloride ($CH_3(CH_2)_{16}COCl$).

8. The method for preparing the pseudo-ceramide compound according to claim 4, further comprising obtaining the compound of Chemical Formula 3 by reacting a compound of Chemical Formula 8 with a compound of Chemical Formula 9 or Chemical Formula 10:

[Chemical Formula 8]

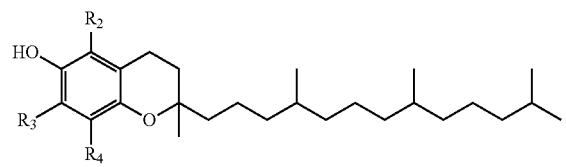

[Chemical Formula 9]

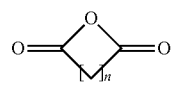

A-X-B    [Chemical Formula 10]

wherein R₂ to R₄ and X have the same definitions as in claim 4, n is 1 or 2, and A and B are the same as or different from each other, and each independently a hydroxyl group, halogen, a C1 to C4 acyloxy group, a C1 to C4 alkyl carbonate group or a C1 to C4 alkoxy group.

9. The method for preparing the pseudo-ceramide compound according to claim 8, wherein the compound of Chemical Formula 9 is succinic anhydride.

10. The method for preparing the pseudo-ceramide compound according to claim 8, wherein the compound of Chemical Formula 10 is chloroacetyl chloride or ethyl bromoacetate.

* * * * *